(12) United States Patent
Petrak et al.

(10) Patent No.: US 11,007,289 B2
(45) Date of Patent: May 18, 2021

(54) METHOD FOR PRESSURIZING A STEAM STERILIZATION CHAMBER

(71) Applicant: American Sterilizer Company, Mentor, OH (US)

(72) Inventors: David Petrak, Mayfield Heights, OH (US); Richard P. Thurman, Newbury, OH (US)

(73) Assignee: American Sterilizer Company, Mentor, OH (US)

(*) Notice: Subject to any disclaimer, the term of this patent is extended or adjusted under 35 U.S.C. 154(b) by 206 days.

(21) Appl. No.: 16/275,908

(22) Filed: Feb. 14, 2019

(65) Prior Publication Data

US 2020/0261609 A1     Aug. 20, 2020

(51) Int. Cl.
*A61L 2/07* (2006.01)

(52) U.S. Cl.
CPC ............. *A61L 2/07* (2013.01); *A61L 2202/14* (2013.01); *A61L 2202/24* (2013.01)

(58) Field of Classification Search
CPC ..... A61L 2/07; A61L 2202/14; A61L 2202/24
See application file for complete search history.

(56) References Cited

U.S. PATENT DOCUMENTS

| 5,876,664 | A | 3/1999 | Childers et al. |
| 9,402,929 | B2 | 8/2016 | Schwartz et al. |
| 9,814,795 | B2 | 11/2017 | Dufresne et al. |
| 10,558,227 | B2 * | 2/2020 | Alcala Perez .......... G01F 25/00 |
| 2016/0378101 | A1 | 12/2016 | Leonard |
| 2017/0007731 | A1 | 1/2017 | Sharma |

FOREIGN PATENT DOCUMENTS

| CN | 206039257 U | 3/2017 |
| EP | 0 177 119 A2 | 4/1986 |
| EP | 1 988 929 A1 | 11/2008 |
| WO | WO-2007/099418 A1 | 9/2007 |
| WO | WO-2017/010525 A1 | 1/2017 |

OTHER PUBLICATIONS

International Search Report from corresponding International Patent Application No. PCT/US2020/014528 dated Apr. 15, 2020.

(Continued)

*Primary Examiner* — Timothy C Cleveland
(74) *Attorney, Agent, or Firm* — Kusner & Jaffe

(57) ABSTRACT

A method for pressurizing a sterilization chamber of a steam sterilizer with a controlled rate of pressure change. Pressure is increased in the sterilization chamber by opening a steam-to-chamber valve for a pulse duration during each of a plurality of time PERIODS needed to reach a target pressure value. During each time PERIOD, the steam-to-chamber valve is moved to an open state for the duration of the pulse. An error value indicative of the difference between a Theoretical Pressure and a Measured Pressure is determined at the end of each PERIOD. This error value is used to determine the duration of the pulse for the subsequent PERIOD, thereby maintaining a desired rate of pressure change in the sterilization chamber.

10 Claims, 3 Drawing Sheets

(56) References Cited

OTHER PUBLICATIONS

Written Opinion of the International Search Authority from corresponding International Patent Application No. PCT/US2020/014528 dated Apr. 15, 2020.
Ho, Anthony K., "An Approved Continuing Education Provider Fundamental of PID Control," dated Jan. 1, 2014, XP055679489, https://pdhonline.com/courses/e331/e331content.pdf (retrieved from the internet on Mar. 25, 2020).
Anonymous, "PID Control and Tuning—abearman/sparrow-dev Wiki . GitHub," dated Apr. 11, 2016, XP055679481, https://github.com/abearman/sparrow-dev/wiki/PID-Control-and-Tuning, (retrieved from internet on Mar. 25, 2020).
F. Tessarolo et al., "Current reference devices for hollow instrument loads as defined in standards are not a valid steam penetration test," Central Service (Apr. 2012), pp. 256-260.
Van Doornmalen, J.P.C.M., "Surface steam sterilization: steam penetration in narrow channels," Eindhoven: Technische Universiteit Eindhoven DOI: 10.6100/IR758412 (Jan. 2013).
M. Dion et al., "Steam Sterilization Principles," Pharmaceutical Engineering, (Nov./Dec. 2013), vol. 33, No. 6.
E. Leiss-Holzinger et al., "A Localized Analysis of the Sterilization Process by Direct Steam Monitoring," IEEE Access (Sep. 2017), vol. 5.
"Guide to Steam Sterilization Cycles—Steam Flush Pressure Pulse," (Oct. 2018) website printout from www.steris.com/healthcare/knowledge-center/sterile-processing/guide-to-steam-sterilization-cycles-steam-flush-pressure-pulse.cfm, printout date Jan. 29, 2019.

\* cited by examiner

METHOD FOR PRESSURIZING A STEAM STERILIZATION CHAMBER

FIELD OF THE INVENTION

The present invention relates generally to a method for operating a steam sterilizer, and more particularly to a method for pressurizing the sterilization chamber of a steam sterilizer to achieve a target pressure level in the chamber.

BACKGROUND OF THE INVENTION

Steam sterilizers are commonly used in healthcare settings to sterilize medical devices. The items to be sterilized are placed inside a pressure vessel, commonly referred to as the sterilization chamber. Three factors are critical to ensuring successful steam sterilization in a steam sterilizer: time, temperature, and steam quality. To meet these requirements there are three (3) phases to a sterilization cycle, namely, a conditioning phase ("Phase I"), a sterilization (or exposure) phase ("Phase II"), and an exhaust phase ("Phase III").

Since air inhibits sterilization it must be removed from the chamber during the conditioning phase of the sterilization cycle. One common approach for air removal in a dynamic air removal-type steam sterilizer is to apply a series of pressurizations with injections of steam (i.e., pressure pulses) and evacuations of the chamber using a vacuum system (i.e., vacuum pulses). After the air is removed from the chamber, the sterilizer drain closes and steam is continuously admitted into the chamber, rapidly increasing the pressure and temperature inside the chamber to a predetermined level. This process step is referred to as "charging" the chamber. Once charging is completed, the sterilization cycle enters the sterilization phase and articles are held at the sterilization temperature for a fixed amount of time required to sterilize a load of articles in the chamber. During the exhaust phase of the sterilization cycle, the sterilizer drain is opened and steam is removed, depressurizing the chamber and allowing the articles in the load to dry.

U.S. Government and International standards on steam sterilization (ANSI/AAMI STS, ISO 17655-1, EN285) require steam sterilizers to validate their performance against established performance criteria to be used in hospitals. The most difficult performance criteria to meet are: (1) temperature uniformity across the chamber and processed load during the sterilization phase and (2) steam density uniformity in the hollow load steam penetration test. It has been shown that the hollow load steam penetration test is sensitive to the "rate" of steam admission to the chamber, and that temperature deviations during the sterilization cycle will vary depending on the contents of the chamber. Therefore, in order to provide a sterilization cycle that reliably and consistently complies with U.S. Government and international standards for steam sterilization, an automatic feedback control involving key parameter(s) involved in steam sterilization performance is needed.

Existing control schemes are ON/OFF control and temperature-based Proportional-Integral-Derivative (PID) control. ON/OFF control requires extensive testing to identify correct values for the parameters. Once identified, the parameter values are only as reliable as the test method. The test method focuses only on one loading condition (usually an empty chamber) resulting in varying performance with different loads, deviations in initial starting temperature of chamber contents, and the size of the chamber.

For PID control that is based on temperature, it is recognized that temperature sensors are often slow in providing feedback to a control system, therefore making control less accurate and less consistent. In addition, temperature-based PID control often requires an expensive proportionally-controlled valve to modulate the magnitude of steam flow as determined by the control system.

The present invention provides an improved method for pressurizing the chamber of a steam sterilizer that overcomes drawbacks of the prior art.

SUMMARY OF THE INVENTION

In accordance with the present invention, there is provided a method for pressurizing a sterilization chamber of a steam sterilizer with a controlled rate of pressure change, comprising: (a) moving a steam-to-chamber valve to an open state for duration of a pulse during each of a plurality of time PERIODS needed to reach a target pressure value, wherein steam is injected into the chamber from a source of steam when the steam-to-chamber valve is in the open state; (b) determining a first error value after pressurizing the sterilization chamber for a first time PERIOD; (c) adjusting the duration of the pulse for a subsequent time PERIOD based upon the error value; (d) determining a subsequent error value after pressurizing the sterilization chamber for the subsequent time PERIOD; (e) repeating steps (c) and (d) until the target pressure value is reached, wherein each of the error values is determined from a difference between a Theoretical Pressure and a Measured Pressure obtained from a pressure sensor sensing a pressure level in the chamber.

An advantage of the present invention is the provision of a method for pressurizing a sterilization chamber that provides a more accurate and consistent chamber pressurization without the need for adding additional equipment to an existing steam sterilizer.

Another advantage of the present invention is the provision of a method for pressurizing a sterilization chamber that provides substantially consistent control of the pressure in the chamber irrespective of loading conditions, starting temperature conditions, and chamber size.

These and other advantages will become apparent from the following description of illustrated embodiments taken together with the accompanying drawings and the appended claims

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein.

DETAILED DESCRIPTION OF THE INVENTION

Figure 1:
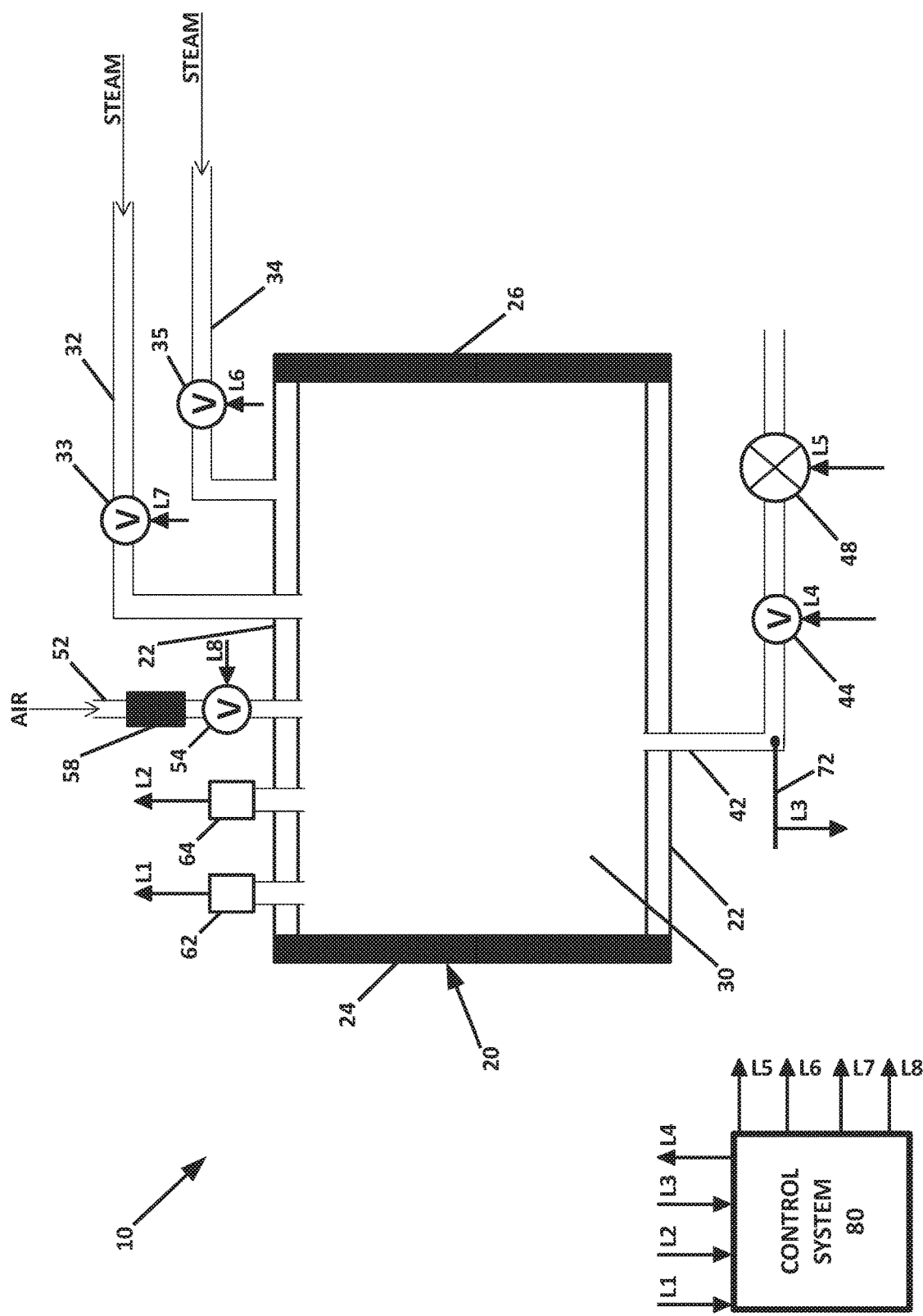
FIG. 1 is a schematic illustration of an exemplary steam sterilizer.

Referring now to the drawings wherein the showings are for the purposes of illustrating an embodiment of the invention only and not for the purposes of limiting same, FIG. 1 is a schematic representation of an exemplary steam sterilizer 10, as used in connection with the method of the present invention. It should be appreciated that sterilizer 10 is shown solely for the purpose of illustrating an embodiment of the present invention, and not for limiting same. Accordingly, it is contemplated that the method of the present invention may be implemented in connection with sterilizers different from illustrated sterilizer 10.

Sterilizer 10 is generally comprised of a housing 20 defining a sterilization chamber 30, a control system 80, a plurality of conduits, a plurality of valves controlled by control system 80, a plurality of sensors providing signals to control system 80, and a vacuum pump 48 controlled by control system 80. Housing 20 is comprised of a double wall jacket 22, a loading door 24 to load chamber 30 and an unloading door 26 to unload chamber 30. Doors 24 and 26 are controlled by control system 80. In some embodiments of sterilizer 10 there is only a single door for loading and unloading chamber 30. The plurality of conduits include a steam inlet conduit 32 in fluid communication with chamber 30 and having a valve 33 disposed therein; a steam inlet conduit 34 in fluid communication with double wall jacket 22 and having a valve 35 disposed therein; an air inlet conduit 52 in fluid communication with chamber 30 and having a valve 54 and a filter 58 disposed therein; and a drain conduit 42 in fluid communication with chamber 30 and having a drain valve 44 disposed therein. The plurality of sensors include a first pressure sensor 62, a second pressure sensor 64, and a pair of temperature sensors 72. Vacuum pump 48 is installed in drain conduit 42 to pump gases and possibly water condensate out of chamber 30.

Steam inlet conduits 32 and 34 are connected to a supply of steam (not shown). The steam supply for sterilizer 10 may be provided by a central boiler in a facility or by a dedicated steam generator. Steam is injected into jacket 22 via steam inlet conduit 34 in order to heat up the inner side of jacket 22. Control system 80 controls valve 35 in order to control the supply of steam to jacket 22. By keeping jacket 22 at a temperature of about 0.5° C. to 1° C. higher than the temperature of chamber 30, no condensation forms on jacket 22. Steam is supplied to chamber 30 via steam inlet conduit 32. Control system 80 controls valve 33 in order to control the supply of steam to chamber 30. It should be appreciated that valves 33 and 35 are independently controlled by control system 80.

Valve 44 is disposed in drain conduit 42 between chamber 30 and vacuum pump 48 in order to prevent potentially contaminated water, vapor, or gas to flow back into chamber 30 through drain conduit 42. When air is injected into chamber 30 via air inlet conduit 52, it is filtered by filter 58 (e.g., a High-Efficiency Particulate Air (HEPA)) to avoid re-contamination of loads.

Pressure sensors 62 and 64 sense pressure in chamber 30 and two temperature sensors 72 are mounted in drain conduit 42. One pressure sensor and one temperature sensor form a set. One set of pressure/temperature sensors is used as control sensors for controlling sterilizer 10. The second set of pressure/temperature sensors is used as monitoring sensors for independent monitoring of pressure and temperature to ensure that the sterilization process is operating correctly. The outputs of the monitoring and control sensors may be presented to a user in a display or visual indicators (not shown) on sterilizer 10.

Control system 80 receives input signals from the sensors 62, 64, and 72, and transmits output signals to the valves 33, 35, 44, and 54, vacuum pump 48, and doors 24, 26. Control system 80 is programmed to control sterilizer 10 during the sterilization cycle.

In accordance with the present invention, a form of PID control is used to control a variable at a moving value. For a steam sterilizer, pressure and temperature are important physical indicators of sterilizer performance. As pressure sensors can be controlled easier, are more accurate, and typically faster than temperature sensors, the sterilizer pressure is preferably used as the control variable according to the method of the present invention.

During any period in which flow via steam is induced, a change of pressure in chamber 30 occurs. To maintain consistent performance from one load to another or from one set of chamber conditions to another, a substantially consistent change in pressure is desired during periods of chamber pressurization. In accordance with the method of the present invention, a form of PID-based control is used to control the chamber pressure to a pressure profile that satisfies appropriate performance criteria from U.S. Government and International standards on steam sterilization.

Figure 2:
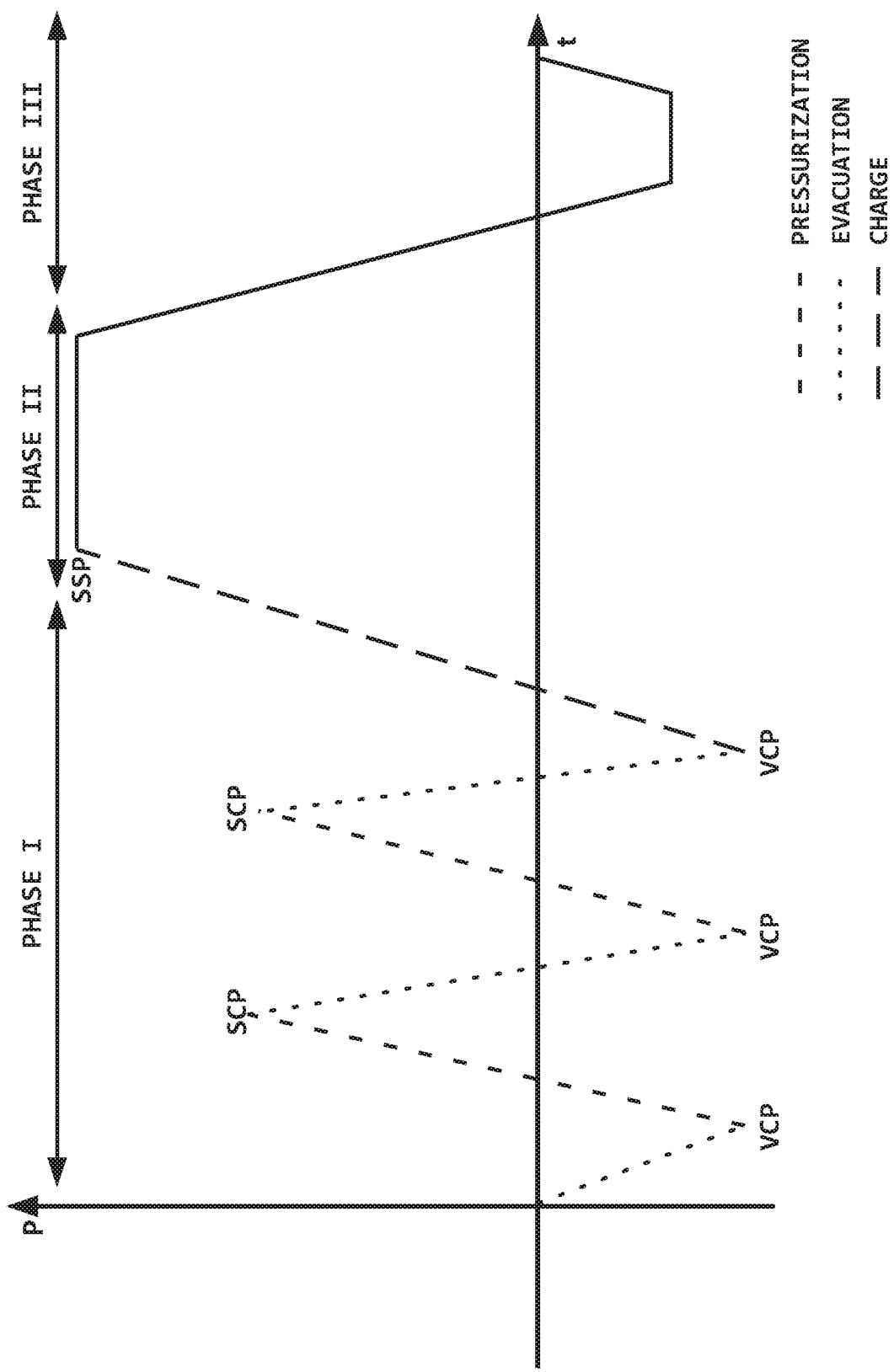
FIG. 2 is a graph showing pressure (P) vs. time (t) during the conditioning phase, the sterilization phase, and the exhaust phase of a sterilization cycle.

Referring now to FIG. 2, there is shown a graph showing pressure vs. time for the three (3) phases of a sterilization cycle for a steam sterilizer, as used to sterilize a process challenge device (PCD) for a hollow instrument load. The short dashed lines are indicative of pressurization, the dotted lines are indicative of evacuation, and the long dashed line is indicative of charge.

In the conditioning phase (Phase I) of the sterilization cycle, control system 80 removes air from the sterilization chamber by applying alternating (i) pressurization with steam injection and (ii) evacuation of the chamber using a vacuum pump. Each vacuum control point (VCP) is indicative of the end of an evacuation phase, and each steam control point (SCP) is indicative of the end of a pressurization phase. For example, each VCP could be set to a level in the range of 5-40 KPA (0.725-4.4 PSIA), while each SCP could be set to a level in the range of 100-300 KPA (14.5-43.5 PSIA). In the illustrated graph, there are two (2) evacuation phases, two (2) pressurization phases, and one (1) charge phase. The last pressurization phase is followed by the charge phase wherein control system 80 pressurizes chamber 30 with steam to a desired pressure level (e.g., 43.5 PSIA) that is suitable for the sterilization phase (Phase II), which begins at the steam sterilization point (SSP). The SSP indicates a transition from the conditioning phase to the sterilization phase.

During the sterilization phase, control system 80 maintains a substantially constant pressure level in chamber 30. The time period for the sterilization phase is the amount of time required to sterilize articles in chamber 30. After the sterilization phase is completed, control system 80 reduces the pressure in chamber 30 during the initial part of the exhaust phase (Phase III). At the end of the exhaust phase, control system 80 fills chamber 30 with filtered air by opening air valve 54, thereby bringing the pressure in chamber 30 to the level of atmospheric pressure (e.g., 14.7 PSIA). During the exhaust phase, control system 80 opens drain valve 44, thereby removing steam from chamber 30 to depressurize chamber 30, and allow the articles in the load to dry.

Control system 80 of the present invention is programmed to repeatedly transition the conditions in chamber 30 between evacuation (a vacuum pulse) and pressurization (pressure pulses) in Phase I (conditioning phase) of the sterilization cycle. FIG. 2 shows a series of pressurization phases and evacuation phases (defined by the vacuum control points (VCPs) and steam control points (SCPs)), followed by a pressurization charge phase that ends at the steam sterilization point (SSP). Control system 80 increases the pressure in chamber 30 during the pressurization and charge phases by opening the steam-to-chamber valve 33 for a predetermined amount of time during each of a plurality of PERIODS. The solid line in FIG. 3 shows the Measured Pressure in chamber 30, while the broken line in FIG. 3 shows a desired Theoretical Pressure in chamber 30.

Figure 3:
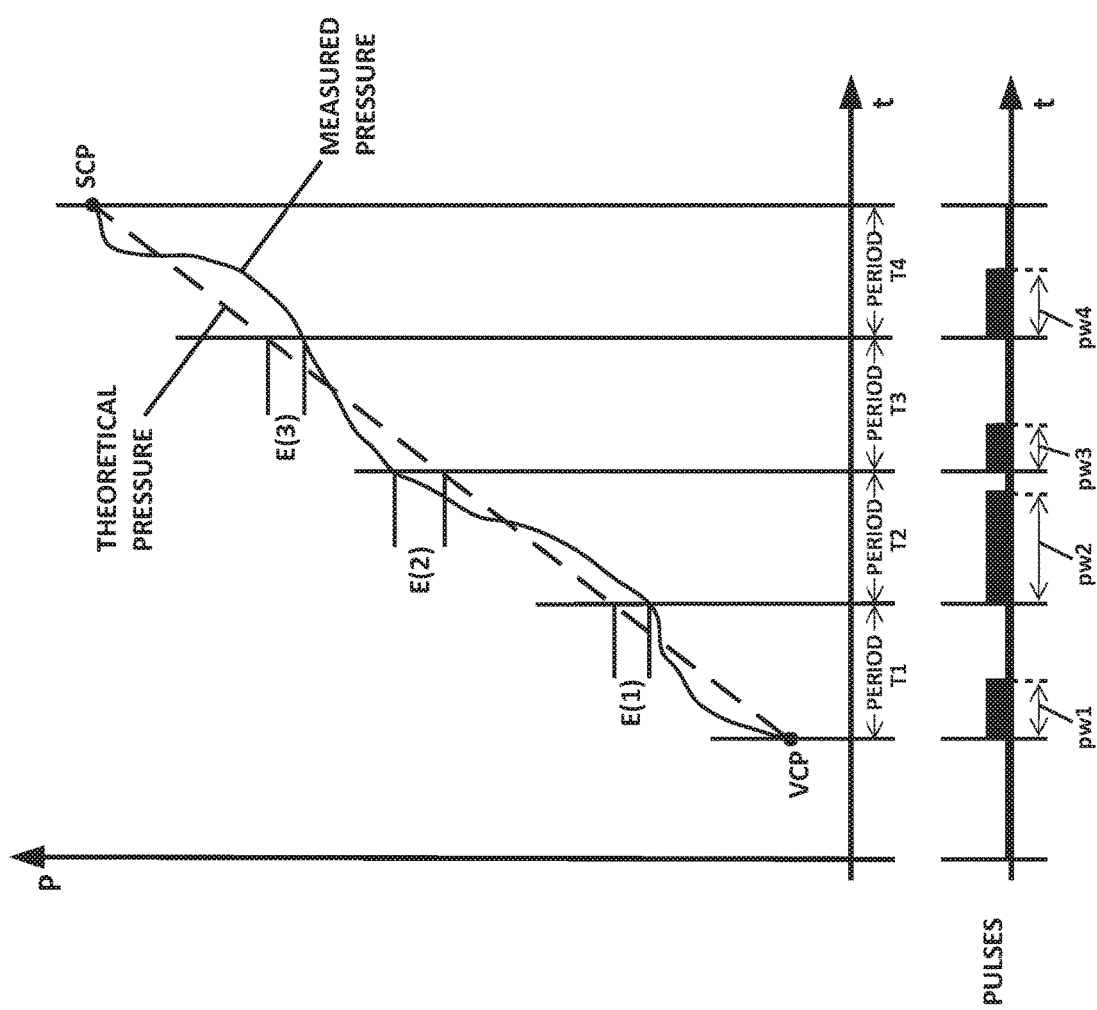
FIG. 3 shows (i) a graph of the theoretical pressure and measured pressure during a time period between a vacuum control point (VCP) and a steam control point (SCP) of the conditioning phase, and (ii) the pulses generated by the control system for opening a valve to fill a sterilization chamber with steam during said time period.

FIG. 3 provides a graph showing a detailed view of a pressurization phase of the conditioning phase divided into a plurality of PERIODS, and a graph showing pulsed operation of the steam-to-chamber valve 33 during each of the plurality of PERIODS. In the pressurization phase illustrated by FIG. 3, there are shown four (4) PERIODS (labelled as T1, T2, T3, and T4) needed to reach the SCP. It should be appreciated that the number of PERIODS for the pressurization and charge phases will be the number of PERIODS respectively needed to reach the SCP or SSP, which are target pressure values. Accordingly, for each pressurization and charge phase, control system 80 controls pulsing of the steam-to-chamber valve 33 during the number of PERIODS needed to reach the pressure level of the SCP or SSP in chamber 30. In the illustrated embodiment, each of the PERIODS of the pressurization and charge phases is of equal time. The length of the PERIOD may be user-defined.

For each PERIOD (T1-T4), control system 80 determines a duration of the pulse during which the steam-to-chamber valve 33 remains in the open state. At the end of the PERIOD, pressure sensor 62 provides a signal to control system 80 indicative of the Measured Pressure in chamber 30. Control system 80 is programmed to compare the Measured Pressure to a Theoretical Pressure that is determined according to equation (1), as shown below:

$$\text{Theoretical Pressure} = \text{Previous Pressure} + \frac{(\text{PERIOD} \times \text{RATE})}{1000} \quad (1)$$

where RATE is a user-defined parameter for the rate of pressure change, and Previous Pressure is the Measured Pressure determined for the prior PERIOD. For the first PERIOD T1, the Previous Pressure is the pressure at the vacuum control point (VCP). The difference between the Theoretical Pressure (as indicated by the broken line at the end of PERIOD T1) from the Measured Pressure (as indicated by the solid line at the end of PERIOD T1) is the error value (E). If the absolute value of the error value (E) is greater than zero, then control system 80 determines how long to maintain steam-to-chamber valve 33 in the open state (i.e., the Pulse Width) during the next PERIOD (e.g., PERIOD T2), according to equation (2) shown below:

$$\text{Pulse Width} = \frac{K_p E + K_d \frac{\Delta E}{\Delta t} + K_i (E_{i-1} + \Delta E \Delta t)}{\text{Bias}} \times \text{PERIOD}; \quad (2)$$

$$\{\text{Min\_P} \leq \text{Pulse Width} \leq \text{Max\_P}\}$$

where $K_p$, $K_d$, and $K_i$ are user-defined parameters referred to in the art as proportional, derivative, and integral constants, respectively. Each of the constants $K_p$, $K_d$, and $K_i$ influences the Pulse Width. $K_p$ commands an action proportional to the error, $K_d$ commands an action proportional to the rate at which the error (E) changes from one measured error sample to the next measured error sample, and $K_i$ commands an action proportional to the rate the error (E) changes over multiple error samples. In addition to these constants, Bias is a user-defined parameter that compensates the overall Pulse Width to mitigate steady-state errors that may occur over time.

If the determined Pulse Width is less than a user-defined minimum pulse width (Min_P) or greater than a user-defined maximum pulse width (Max_P), then control system 80 sets Pulse Width to the nearest value (Min_P or Max_P). In one embodiment of the present invention, Max_P is equal to PERIOD.

At the end of PERIOD T2, control system 80 re-computes equations (1) and (2) to determine the Pulse Width for PERIOD T3. For equation (1), the value of the Measured Pressure determined for PERIOD T1 is used as the Previous Pressure. Control system 80 repeats this process until the pressure in chamber 30 reaches the steam control point (SCP), as shown in FIG. 2. Control system 80 also operates in a similar manner during the charge phase to obtain a pressure in chamber 30 that reaches the steam sterilization point (SSP).

Equations (1) and (2) shown above apply for each positive pressure change within Phase I of the sterilization process, which are shown in FIG. 2 as the short dashed lines (pressurization) and the long dashed lines (charge).

It should be appreciated that the value of all parameters described above as "user-defined" are programmable into control system 80 to provide predetermined values for the parameters.

As indicated above, the number of PERIODS will be affected by (i) the length of the PERIOD, and (ii) the amount of time needed to reach a target pressure value. In the example shown in FIG. 3, four (4) PERIODS are needed to pressurize chamber 30 from the VCP to the SCP.

Laboratory tests from over 150 experiments performed on a prototype steam sterilizer revealed an error of 0.58% when using the following parameters in equation (1) when RATE is between 35 and 100 kPa/min:

| Kp | Ki | Kd | Bias | PERIOD (ms) |
|---|---|---|---|---|
| 2.7 | 5.0 | 10.0 | 137 | 1200 |
| 2.7 | 5.0 | 10.0 | 205 | 1800 |
| 2.7 | 5.0 | 10.0 | 274 | 2400 |
| 2.7 | 5.0 | 10.0 | 343 | 3000 |
| 2.7 | 5.0 | 10.0 | 550 | 4800 |

At the start of Phase II (sterilization phase), identified as the steam sterilization point (SSP) in FIG. 2, control system 80 replaces RATE in equation (1) with the sterilization pressure (SP). Therefore, in Phase II equation (1) is replaced with equation (1A), as shown below:

$$\text{Theoretical Pressure} = \text{Previous Pressure} + \frac{(\text{PERIOD} \times SP)}{1000} \quad (1A)$$

where
Previous Pressure is the Measured Pressure determined in a prior PERIOD or a pressure at the steam sterilization point (SSP).

Control system 80 determines the sterilization pressure (SP) according to equation (3), shown below:

$$SP = P_c \times \exp\left(\left(\frac{T_c}{T_s + \text{overdrive}}\right) \cdot \right.$$
$$\left. [b_1 E + b_2 E^{1.5} + b_3 E^3 + b_4 E^{3.5} + b_5 E^4 + b_6 E^{7.5}]\right) \quad (3)$$

where:

$$E = 1 - T_s/T_c$$

and the values of the respective constants are as follows:
$T_s$=sterilization temperature (121° C. or 134° C., depending on selected cycle),
overdrive=user-defined number of degrees C. above $T_s$,
$T_c$=measured temperature (in Celsius) in the drain conduit,
$P_c$=22.064 MPa (i.e., the critical point pressure of water),
$b_1$=−7.85951783,
$b_2$=1.84408259,
$b_3$=−11.7866497,
$b_4$=22.6807411,
$b_5$=−15.9618719, and
$b_6$=1.80122502.

It should be noted that $T_c$ is a measured temperature, as sensed by a temperature sensor (e.g., an RTD probe) located in the drain conduit. In one embodiment of the present invention there is a 20 second stabilization period prior to the start of the sterilization phase (e.g., at 3-5 PSIA below SSP). During this stabilization period, the control system allows the temperature and pressure to stabilize in order to calculate a stable and accurate value for $T_c$.

In accordance with one embodiment of the present invention, equation (3) may take the following form:

$$SP = \exp(-3892.70/(T_c - 42.6776 + 273.15) + 9.486540)/0.000133322$$

where:
$T_c$=measured temperature in Celsius+overdrive, wherein $T_c$ is measured and recorded in real time by use of a temperature sensor (e.g., an RTD probe) located in the drain conduit of the steam sterilizer, and overdrive is a software variable.

In Phase II, a different set of values for $K_p$, $K_d$, $K_1$, Bias, and PERIOD are used in equations (1) and (2) to ensure temperature requirements from the standards are met and because pressure changes are less drastic over time during Phase II than in Phase I of the sterilization cycle shown in FIG. 2. In particular, during Phase II control system 80 controls valve 33 to regulate the supply of steam to chamber 30 in the same manner as in Phase I, except the goal is to regulate the pressure in chamber 30 at a calculated theoretical pressure (i.e., a fixed setpoint pressure).

In accordance with the method of the present invention, the pressure in chamber 30 is substantially maintained at a user-defined rate of change, thus facilitating a consistent sterilization process from one sterilization cycle to the next sterilization cycle, irrespective of physical changes internal or external to chamber 30.

It should be appreciated that while the present invention has been described with reference to a steam sterilizer it is contemplated that the present invention finds utility with any decontamination apparatus used to disinfect or sterilize medical devices with narrow channels by means of a chemical, gas, and/or fluid whose composition is directly influenced by changes in physical parameters, such as pressure and/or temperature. It is also contemplated that the method of the present invention can be adapted to modulate the action of a flow-inducing element according to the difference between the desired rate of temperature change and the measured rate of temperature change.

The foregoing describes specific embodiment(s) of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method for pressurizing a sterilization chamber of a steam sterilizer with a controlled rate of pressure change, comprising:
   (a) moving a steam-to-chamber valve to an open state for duration of a pulse during each of one or more time PERIODS needed to reach a target pressure value;
   (b) determining a first one of one or more error values after pressurizing the sterilization chamber for a first one of the time PERIODS;
   (c) adjusting the duration of the pulse for a subsequent one of the time PERIODS, the duration of the pulse for the subsequent one of the time PERIODS being based upon the first one of the error values if the adjusting of the duration is performed after the determining of the first one of the error values, the duration of the pulse for the subsequent one of the time PERIODS being based upon a subsequent one of the error values if the subsequent one of the error values has been determined;
   (d) determining the subsequent one of the error values after pressurizing the sterilization chamber for the subsequent one of the time PERIODS; and
   (e) repeating steps (c) and (d) until the target pressure value is reached,
   wherein the first one of the error values is determined from a difference between a Theoretical Pressure and a Measured Pressure obtained from a pressure sensor sensing a pressure level in the chamber after pressurizing the sterilization chamber for the first one of the time PERIODS,
   wherein the subsequent one of the error values is determined from a difference between a Theoretical Pressure and a Measured Pressure obtained from the pressure sensor sensing the pressure level in the chamber after pressurizing the sterilization chamber for the subsequent one of the time PERIODS,
   wherein steam is injected into the chamber from a source of steam when the steam-to-chamber valve is in the open state, and
   wherein each of said time PERIODS is of equal time.

2. The method according to claim 1, wherein said Theoretical Pressure is determined by a control system according to the following expression:

$$\text{Theoretical Pressure} = \text{Previous Pressure} + \frac{(\text{PERIOD} \times \text{RATE})}{1000}$$

where
PERIOD is the duration of each of the time PERIODS,
RATE is the controlled rate of pressure change, and
Previous Pressure is the Measured Pressure determined in a prior one of the time PERIODS a pressure at a vacuum control point (VCP).

3. The method according to claim 2, wherein, if, after pressurizing the sterilization chamber for a first one of the time PERIODS, an absolute value of said first one of said error values is greater than zero, then the duration of said pulse for the subsequent one of the time PERIODS based upon the first one of the error values is defined by a Pulse Width according to the following expression:

$$\text{Pulse Width} = \frac{K_p E + K_d \frac{\Delta E}{\Delta t} + K_i (E_{i-1} + \Delta E \Delta t)}{\text{Bias}} \times \text{PERIOD}$$

where
  $K_p$ is a user-defined proportional constant,
  $K_d$ is a user-defined derivative constant,
  $K_i$ is a user-defined integral constant,
  E is the error value, $$\frac{\Delta E}{\Delta t}$$

is a rate at which the error value changes from each measured error sample,
  $(E_{i-1} + \Delta E \Delta t)$ is rate the error value changes over multiple error samples, and
  Bias is a user-defined parameter compensating Pulse Width to mitigate steady-state errors, and
wherein, if, after pressurizing the sterilization chamber for the subsequent one of the time PERIODS, an absolute value of said subsequent one of the error values is greater than zero, then the duration of said pulse for the subsequent one of the time PERIODS based upon the subsequent one of the error values is defined by a Pulse Width according to the following expression:

$$\text{Pulse Width} = \frac{K_p E + K_d \frac{\Delta E}{\Delta t} + K_i (E_{i-1} + \Delta E \Delta t)}{\text{Bias}} \times \text{PERIOD}$$

where
  $K_p$ is a user-defined proportional constant,
  $K_d$ is a user-defined derivative constant,
  $K_i$ is a user-defined integral constant,
  E is the error value, $$\frac{\Delta E}{\Delta t}$$

is a rate at which the error value changes from each measured error sample,
  $(E_{i-1} + \Delta E \Delta t)$ is rate the error value changes over multiple error samples, and
  Bias is a user-defined parameter compensating Pulse Width to mitigate steady-state errors.

4. The method according to claim 3, wherein,
  if the Pulse Width is less than a minimum pulse width (Min_P), then the Pulse Width is set to Min_P, and
  wherein if the Pulse Width is greater than said PERIOD, then the Pulse Width is set to Max_P.

5. The method according to claim 4, wherein Max_P is equal to PERIOD.

6. The method according to claim 1, wherein pressure is increased in the chamber during the time PERIODS, the time PERIODS beginning at a vacuum control point (VCP) and ending at a steam control point (SCP).

7. The method according to claim 1, wherein pressure is increased in the chamber during the time PERIODS, the time PERIODS beginning at a vacuum control point (VCP) and ending at a steam sterilization point (SSP).

8. The method according to claim 1, wherein the target pressure value is defined by a steam control point (SCP).

9. The method according to claim 1, wherein the target pressure value is defined by a steam sterilization point (SSP).

10. The method according to claim 1, wherein said Theoretical Pressure is determined by a control system according to the following expression:

$$\text{Theoretical Pressure} = \text{Previous Pressure} + \frac{(\text{PERIOD} \times SP)}{1000}$$

where
  PERIOD is the duration of each of the time PERIODS,
  RATE is a rate of pressure change,
  SP is Sterilization Pressure, and
  Previous Pressure is the Measured Pressure determined in a prior PERIOD or a pressure at a steam sterilization point (SSP), and
wherein the Sterilization Pressure (SP) is determined by the control system according to the following expression:

$$SP = P_c \times \exp\left(\left(\frac{T_c}{T_s + \text{overdrive}}\right) \cdot [b_1 E + b_2 E^{1.5} + b_3 E^3 + b_4 E^{3.5} + b_5 E^4 + b_6 E^{7.5}]\right)$$

where:
  $E = 1 - T_s/T_c$,
  $T_c$ = sterilization temperature in Celsius,
  overdrive = user-defined number of degrees ° C. above $T_s$,
  $T_c$ = a measured temperature in Celsius,
  $P_c$ = critical point pressure of water in MPa,
  $b_1 = -7.85951783$,
  $b_2 = 1.84408259$,
  $b_3 = -11.7866497$,
  $b_4 = 22.6807411$,
  $b_5 = -15.9618719$, and
  $b_6 = 1.80122502$.

* * * * *